US011320442B2

(12) United States Patent
Kang et al.

(10) Patent No.: US 11,320,442 B2
(45) Date of Patent: *May 3, 2022

(54) DETECTION OF AGGREGATED PROTEINS ASSOCIATED WITH NEURODEGENERATIVE DISEASE USING A PHOTOOXIDATION-INDUCED AMPLIFICATION IMMUNOASSAY

(71) Applicant: KOREA INSTITUTE OF SCIENCE AND TECHNOLOGY, Seoul (KR)

(72) Inventors: Ji Yoon Kang, Seoul (KR); Min Cheol Park, Seoul (KR); Youhee Heo, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/491,184

(22) Filed: Apr. 19, 2017

(65) Prior Publication Data
US 2017/0307638 A1 Oct. 26, 2017

(30) Foreign Application Priority Data

Apr. 20, 2016 (KR) .......................... 10-2016-0048235

(51) Int. Cl.
*G01N 33/68* (2006.01)
*C12N 13/00* (2006.01)

(52) U.S. Cl.
CPC ......... *G01N 33/6896* (2013.01); *C12N 13/00* (2013.01); *G01N 2333/4709* (2013.01);
(Continued)

(58) Field of Classification Search
CPC ....... G01N 33/6896; G01N 2800/2821; G01N 2800/2828; G01N 2800/2835;
(Continued)

(56) References Cited

U.S. PATENT DOCUMENTS

| 8,916,341 B1* | 12/2014 | Bystryak | G01N 33/542 |
| | | | 435/4 |
| 2010/0009388 A1* | 1/2010 | An | G01N 33/6896 |
| | | | 435/7.9 |
| 2013/0130288 A1* | 5/2013 | Goure | G01N 33/6896 |
| | | | 435/7.94 |

OTHER PUBLICATIONS

Fukumoto H et al. Age but not diagnosis is the main predictor of plasma amyloid beta-protein levels. Arch. Neurol. 60, 958-964. (Year: 2003).*

(Continued)

*Primary Examiner* — Kimberly Ballard
(74) *Attorney, Agent, or Firm* — Golidlocks Zone IP Law

(57) ABSTRACT

Disclosed is a method for body fluid-based neurodegenerative disease diagnosis through high-sensitive immunoassay of aggregated proteins by photooxidation-induced amplification. The method according to the present disclosure provides an effect of quantitatively analyzing aggregated proteins in the form of oligomers or monomers which are present in trace amounts in a body fluid and measures normal or abnormal protein aggregation by detecting the aggregated proteins in the form of oligomers or monomers with high sensitivity by reaction of antibody-conjugated enzymes selectively bound to the aggregated proteins with substrates and photooxidation-induced amplification, thereby allowing accurate diagnosis of a neurodegenerative disease.

11 Claims, 8 Drawing Sheets

(52) U.S. Cl.
CPC ............... *G01N 2800/2821* (2013.01); *G01N 2800/2828* (2013.01); *G01N 2800/2835* (2013.01); *G01N 2800/7047* (2013.01)

(58) Field of Classification Search
CPC ..... G01N 2800/7047; G01N 33/54306; G01N 33/542; G01N 33/533; G01N 33/582; C12Q 1/28; C12N 13/00
See application file for complete search history.

(56) References Cited

OTHER PUBLICATIONS

Kosaka T et al. The betaAPP717 Alzheimer mutation increases the percentage of plasma amyloid-beta protein ending at Abeta42(43). Neurology, 48, 741-745. (Year: 1997).*

Kuo YM et al. Amyloid-beta peptides interact with plasma proteins and erythrocytes: Implications for their quantitation in plasma. Biochem. Biophys. Res. Comm. 268, 750-756. (Year: 2000).*

Lobb RJ et al. Optimized exosome isolation protocol for cell culture supernatant and human plasma. J. Extracellular Vesicles, 4: 27031, pp. 1-11. (Year: 2015).*

Tamaoka A et al. Amyloid beta protein in plasma from patients with sporadic Alzheimer's disease. J. Neurol. Sci. 151, 65-68. (Year: 1996).*

Vanderstichele H et al. Standardization of measurement of beta-amyloid 1-42 in cerebrospinal fluid and plasma. Amyloid, 7, 245-258. (Year: 2000).*

Zhao B et al. Photooxidation of Amplex red to resorufin: Implications of exposing the Amplex red assay to light. Free Radical Biol. Med. 53, 1080-1087. (Year: 2012).*

Zhao L et al. Plasma amyloid-beta oligomers level is a biomarker for Alzheimer's disease diagnosis. Biochem. Biophys. Res. Comm. 423, 697-702. (Year: 2012).*

Fiandaca MS et al. Identifcation of preclinical Alzheimer's disease by a profile of pathogenic proteins in neurally derived blood exosomes: A case-control study. Alzheimer's & Dementia, 11, 600-607. (Year: 2015).*

Campa, M. Molecular Probes' Amplex Red online review, Feb. 2004; retrieved from www.biocompare.com/Product-Reviews/40683-Molecular-Probes-Amplex-Red/ on Jun. 9, 2019 (Year: 2004).*

Human Abeta42 ELISA Kit product sheet, Invitrogen, Jan. 22, 2018, 4 pages. (Year: 2018).*

Xia W et al. A specific enzyme-linked immunosorbent assay for measuring beta-amyloid protein oligomers in human plasma and brain tissue of patients with Alzheimer disease. Arch Neurol. 66(2):190-199. (Year: 2009).*

Held, P. Determination of Horseradish Peroxidase (HRP) using Amplex® Red and the SynergyTM HT Microplate Reader. BioTek Application Note, Apr. 18, 2003; www.biotek.com/resources/docs/Synergy_HT_Determination_of_Horseradish_Peroxidase.pdf, Retrieved from internet on Sep. 22, 2021. (Year: 2003).*

* cited by examiner

DETECTION OF AGGREGATED PROTEINS ASSOCIATED WITH NEURODEGENERATIVE DISEASE USING A PHOTOOXIDATION-INDUCED AMPLIFICATION IMMUNOASSAY

CROSS-REFERENCE TO RELATED APPLICATIONS

This application claims, under 35 U.S.C. § 119, the priority of Korean Patent Application No. 10-2016-0048235 filed on Apr. 20, 2016 in the Korean Intellectual Property Office, the disclosure of which is incorporated herein by reference in its entirety.

TECHNICAL FIELD

The present disclosure relates to a method for body fluid-based neurodegenerative disease diagnosis, more particularly to a method for neurodegenerative disease diagnosis using high-sensitive immunoassay of aggregated proteins by photooxidation-induced amplification, which quantitavely analyzes aggregated proteins in the form of oligomers or monomers which are present in trace amounts in a body-fluid and measures normal or abnormal protein aggregation by detecting the aggregated proteins in the form of oligomers or monomers with high sensitivity by reaction of antibody-conjugated enzymes selectively bound to the aggregated proteins with substrates and photooxidation-induced amplification, thereby allowing accurate diagnosis of a neurodegenerative disease.

BACKGROUND

Neuronal dysfunction and damage may be induced by toxic, easily aggregatable proteins and a plurality of neurological diseases are characterized by such a condition. These diseases include amyotrophic lateral sclerosis, Alzheimer's disease, Parkinson's disease, prion disease, polyglutamine expansion disease, spinocerebellar ataxia, spinal and bulbar muscular atrophy, spongiform encephalopathy, tauopathy, Huntington's disease or myodystonia.

Therefore, methods for immunoassay of aggregated proteins in the form of oligomers or monomers present in a body fluid through enzyme-linked immunosorbent assay (ELISA) are being reported. The enzyme-linked immunosorbent assay is a quantitative method for detecting antigens or antibodies using enzyme-conjugated antibodies. Usually, the reaction is completed in the wells of a microplate and the antigens or antibodies are quantified by optically measuring the enzyme-substrate reaction using, e.g., a plate reader and comparing the result with reference values.

However, the existing immunoassay of aggregated proteins by enzyme-linked immunosorbent assay is problematic in that accurate quantification is difficult because the aggregated proteins are present in the body fluid in trace amounts. That is to say, the existing immunoassay of aggregated proteins by enzyme-linked immunosorbent assay is problematic in that, if the aggregated proteins are present in trace amounts or at low concentrations, the color change or light emission by the substrate cannot be detected or quantification of the aggregated proteins is impossible even if it can be detected. Accordingly, it is difficult to accurately diagnose neurodegenerative diseases based on normal or abnormal protein aggregation.

SUMMARY

The present disclosure is directed to providing a method for neurodegenerative disease diagnosis using high-sensitive immunoassay of aggregated proteins by photooxidation-induced amplification, which quantitavely analyzes aggregated proteins in the form of oligomers or monomers which are present in trace amounts in a body fluid and measures normal or abnormal protein aggregation by detecting the aggregated proteins in the form of oligomers or monomers with high sensitivity by reaction of antibody-conjugated enzymes selectively bound to the aggregated proteins with substrates and photooxidation-induced amplification, thereby allowing accurate diagnosis of a neurodegenerative disease.

In an aspect, the present disclosure provides a method for neurodegenerative disease diagnosis using high-sensitive immunoassay of aggregated proteins by photooxidation-induced amplification, which includes: a step of preparing a body fluid sample; a step of preparing separately a body fluid sample containing antibody-conjugated enzymes bound to aggregated proteins and a reference sample not containing antibody-conjugated enzymes bound to aggregated proteins; a step of performing an enzyme-substrate reaction of the body fluid sample and the reference sample; after the enzyme-substrate reaction, a step of performing photooxidation-induced amplification by continuously exposing the body fluid sample and the reference sample to light; a step of optically detecting light emission from products during the photooxidation-induced amplification and indexing the photooxidation-induced amplification pattern with time; and a step of analyzing the contents of aggregated proteins in a body fluid by comparing the photooxidation-induced amplification pattern index of the body fluid sample with that of the reference sample, thereby diagnosing a neurodegenerative disease.

The method for neurodegenerative disease diagnosis using high-sensitive immunoassay of aggregated proteins by photooxidation-induced amplification according to the present disclosure provides an effect of quantitatively analyzing aggregated proteins in the form of oligomers or monomers which are present in trace amounts in a body fluid and measures normal or abnormal protein aggregation by detecting the aggregated proteins in the form of oligomers or monomers with high sensitivity by reaction of antibody-conjugated enzymes selectively bound to the aggregated proteins with substrates and photooxidation-induced amplification, thereby allowing accurate diagnosis of a neurodegenerative disease.

DETAILED DESCRIPTION OF EMBODIMENTS

In the present disclosure, for high-sensitive immunoassay of aggregated proteins in the form of oligomers or monomers present in trace amounts in a body fluid, antibody-conjugated enzymes bound to the aggregated proteins are reacted with substrates and the products are detected with high sensitivity through photooxidation-induced amplification. Two kinds of antibodies which recognize the N-terminus or C-terminus of the aggregated proteins may be used to selectively detect the aggregated proteins in the form of oligomers or monomers. By quantifying and analyzing the aggregated proteins in the form of oligomers or monomers present in trace amounts in the body fluid, a neurodegenerative disease can be accurately diagnosed based on normal or abnormal protein aggregation.

Hereinafter, exemplary embodiments of the present disclosure are described in detail referring to the attached drawings.

FIG. 1 schematically describes a step of preparing a body fluid sample containing antibody-conjugated enzymes bound to aggregated proteins according to an exemplary embodiment of the present disclosure.

Figure 1A:
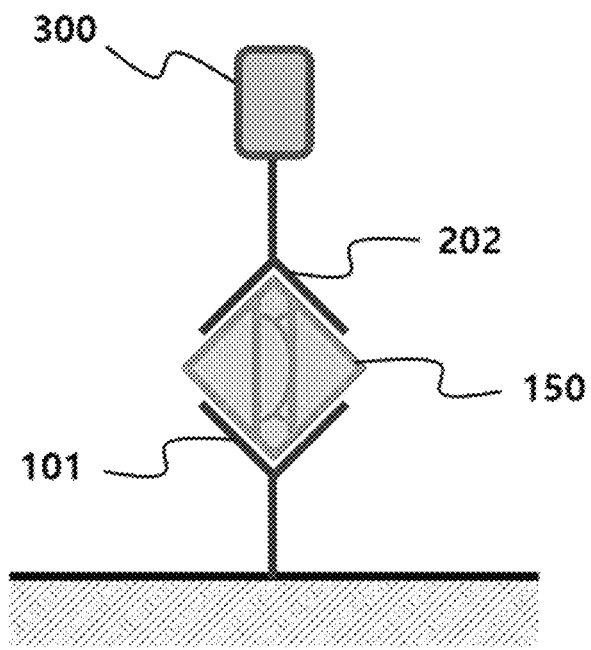
FIGS. 1A and 1B schematically describe a step of preparing a body fluid sample containing antibody-conjugated enzymes bound to aggregated proteins according to an exemplary embodiment of the present disclosure.
Figure 1B:
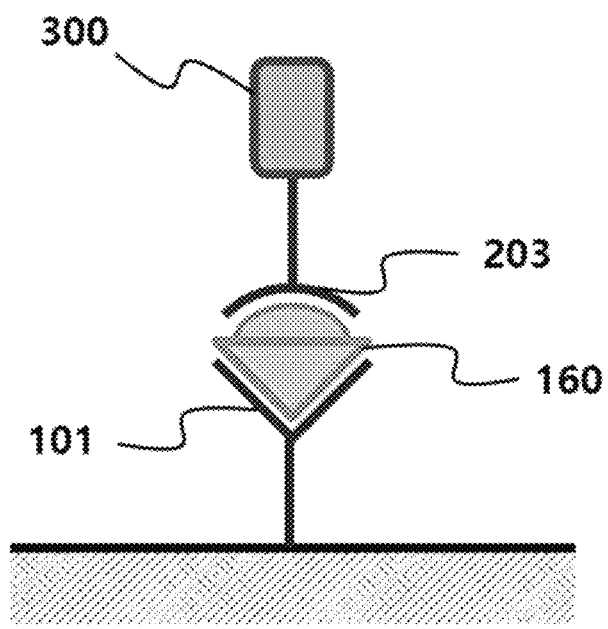

Specifically, FIG. 1A shows an exemplary body fluid sample containing oligomer-type aggregated proteins and FIG. 1B shows an exemplary body fluid sample containing monomer-type aggregated proteins.

As a body fluid sample and a reference sample, a body fluid sample containing antibody-conjugated enzymes bound to aggregated proteins and a reference sample not containing antibody-conjugated enzymes bound to aggregated proteins are prepared separately. Especially, as shown in FIG. 1A and FIG. 1B, a body fluid sample containing antibody-conjugated enzymes selectively bound to oligomer- or monomer-type aggregated proteins is prepared.

For example, the body fluid sample is prepared as follows. After preparing a substrate or magnetic beads onto which primary antibodies 101 recognizing the N-terminus of the aggregated proteins are bound, a body fluid sample is added to the substrate or magnetic beads with the primary antibodies 101 bound thereto and washed with a buffer solution after incubation for a predetermined time (e.g., 15 minutes).

The oligomer-type aggregated proteins 150 are incubated with secondary antibodies 202 recognizing the N-terminus of the aggregated proteins for a predetermined time (e.g., 15 minutes) and washed with a buffer solution.

And, the monomer-type aggregated proteins 160 are incubated with secondary antibodies 203 recognizing the C-terminus of the aggregated proteins for a predetermined time (e.g., 15 minutes) and washed with a buffer solution.

When preparing the body fluid sample containing aggregated proteins, body fluid samples of various concentrations can also be prepared for the oligomer- or monomer-type aggregated proteins.

Next, the secondary antibodies 202, 203 are conjugated with enzymes (e.g., peroxidase) 300 that can react with substrates and washed with a buffer solution. Instead, secondary antibodies 202, 203 already conjugated with enzymes 300 may be used. In this case, the process of enzyme conjugation may be omitted.

Figure 2A:
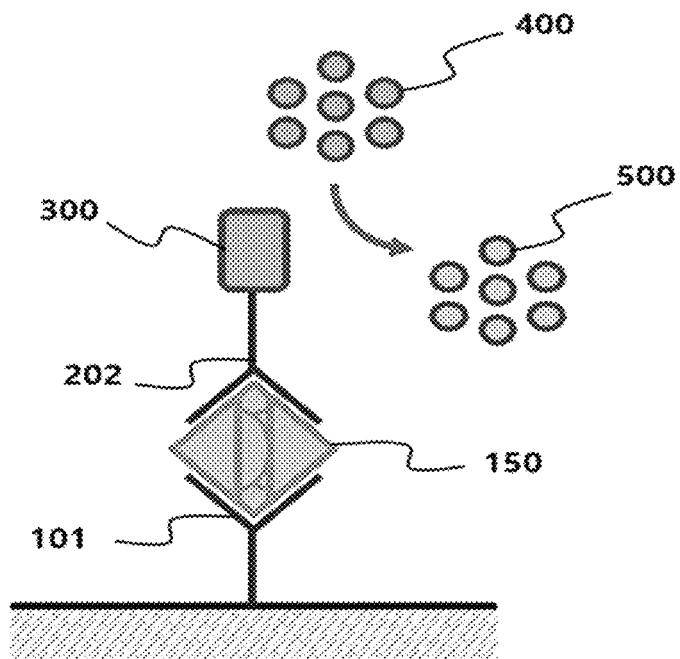
FIGS. 2A and 2B schematically describe an enzyme-substrate reaction in high-sensitive immunoassay according to an exemplary embodiment of the present disclosure.
Figure 2B:
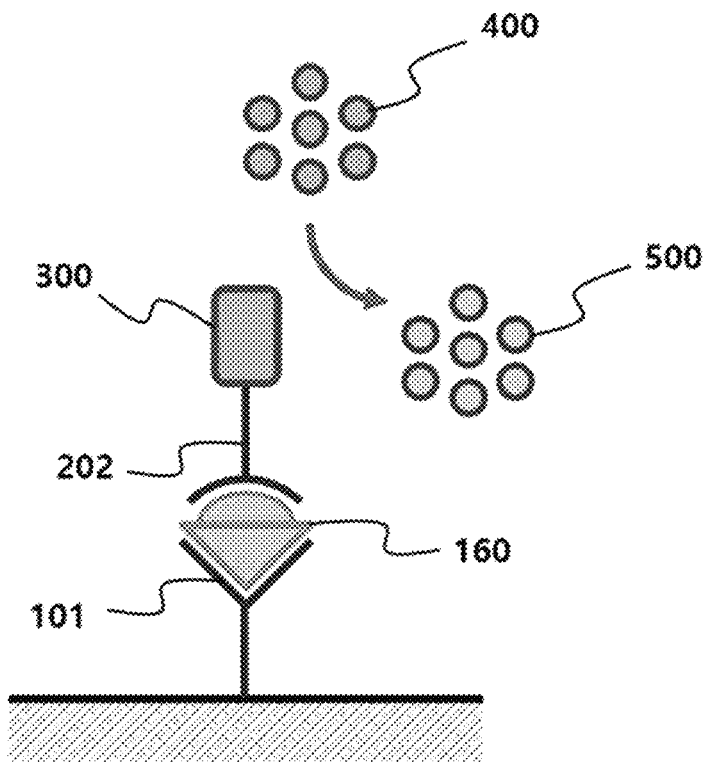

FIGS. 2A and 2B schematically describe an enzyme-substrate reaction in high-sensitive immunoassay according to an exemplary embodiment of the present disclosure.

As seen from FIGS. 2A and 2B, after the body fluid sample containing antibody-conjugated enzymes bound to aggregated proteins in the form of oligomers or monomers and the reference sample not containing antibody-conjugated enzymes bound to aggregated proteins are prepared, the body fluid sample and the reference sample are mixed with a substrate solution to induce an enzyme-substrate reaction.

Specifically, after adding a solution of a substrate that can react with the enzymes to the body fluid sample and the reference sample, an enzyme-substrate reaction is performed for a predetermined time (e.g., 15-30 minutes). For example, ADHP (AMPLEX® Red; 10-acetyl-3,7-dihydroxyphenoxazine) may be used as the substrate. After the enzyme-substrate reaction of the samples, the enzyme-substrate reaction may be stopped by adding a stop solution. However, the following photooxidation-induced amplification process may also be performed after a predetermined time without stopping the enzyme-substrate reaction.

During the enzyme-substrate reaction, the colorless, non-fluorescent substrate (AMPLEX® Red) turns into a product (resorufin) which exhibits color and fluorescence due to the action of the enzymes (peroxidase, 300). The reaction of the oligomer- or monomer-type aggregated proteins can be immunoassayed using the enzyme-substrate reaction. That is to say, the aggregated proteins in the form of oligomers or monomers may be quantified by conjugating enzymes (peroxidase, 300) to the antibodies to which the oligomer- or monomer-type aggregated proteins are selectively bound and measuring the degree of the enzyme-substrate reaction.

However, with the existing enzyme-linked immunosorbent assay, the color change or light emission by the substrate cannot be detected or accurate quantification of the aggregated proteins is impossible even if it can be detected if the aggregated proteins are present in trace amounts or at low concentrations.

In the present disclosure, to solve this problem, the substance exhibiting color or light produced from the enzyme-substrate reaction is amplified to a detectable level through photooxidation-induced amplification and the amplification pattern is indexed to quantify the immune reaction of a sample of low concentration or trace amount, thereby allowing accurate analysis of the immune reaction of the sample of low concentration or trace amount.

Figure 3:
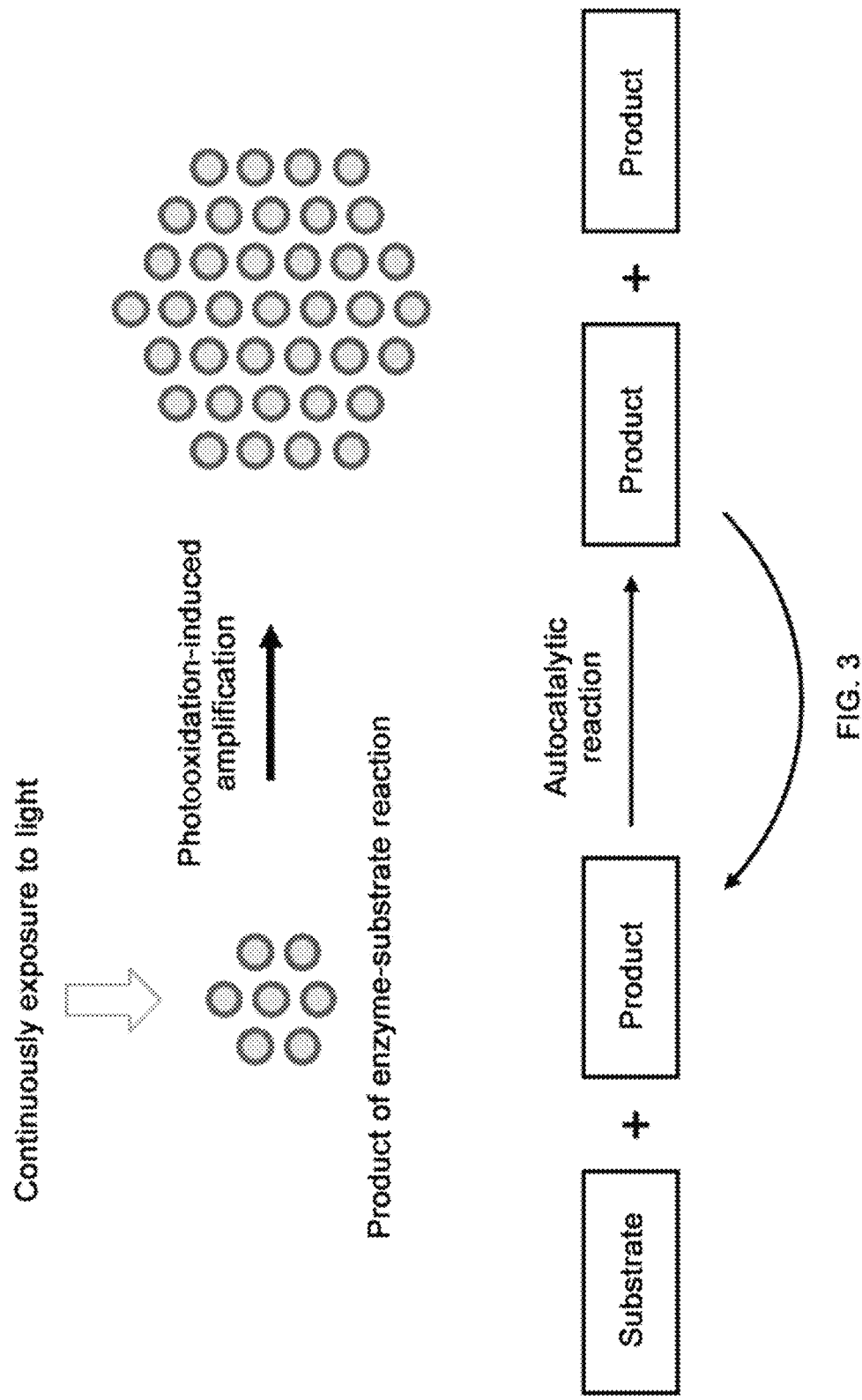
FIG. 3 schematically describes a process of photooxidation-induced amplification by autocatalytic reaction according to an exemplary embodiment of the present disclosure.

FIG. 3 schematically describes a process of photooxidation-induced amplification by autocatalytic reaction according to an exemplary embodiment of the present disclosure.

As seen from FIG. 3, after the enzyme-substrate reaction of the samples is stopped or after a predetermined time, the light emission by the products is optically detected during the photooxidation-induced amplification and its pattern with time is indexed to quantify the concentration of the aggregated proteins.

In other words, an autocatalytic reaction occurs when the samples are subjected to the photooxidation-induced amplification after the enzyme-substrate reaction. That is to say, when the samples are exposed to light after the enzyme-substrate reaction, the amount of the light-emitting substance (resorufin) is amplified through the autocatalytic reaction according to Equation 1. The photooxidation-induced amplification pattern can be plotted by measuring the fluorescence intensity of the light-emitting substance with time.

$$Y = \frac{AR_0 + RSF_0}{1 + \frac{AR_0}{RSF_0}e^{-(AR_0+RSF_0)\times RX}}$$ [Equation 1]

When the color change or light emission of the products is optically detected during the photooxidation-induced amplification, the color change or light emission of the products due to the autocatalytic reaction is measured continuously with time while continuously exposing the body fluid sample and the reference sample to light. For this, video images may be recorded while continuously exposing to light or measurement may be made with time while intermittently exposing to light with short time intervals.

Figure 4:
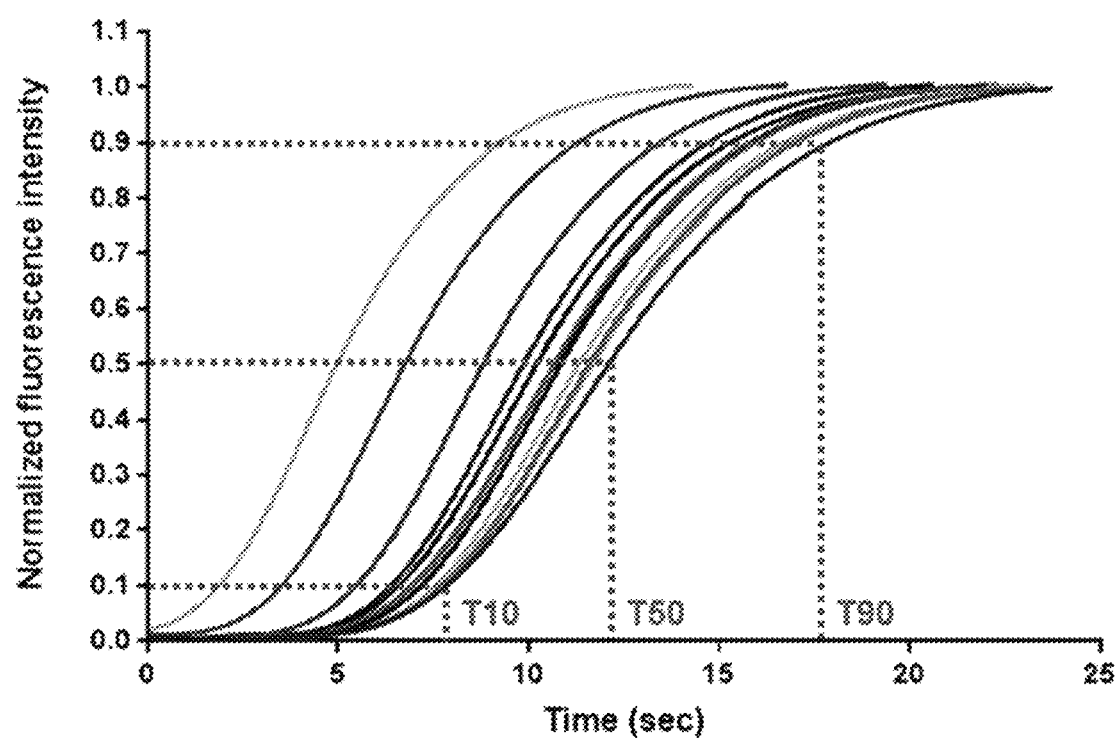
FIG. 4 shows a result of photooxidation-induced amplification and indexing depending on enzyme concentrations according to an exemplary embodiment of the present disclosure.

FIG. 4 shows a result of photooxidation-induced amplification and indexing depending on enzyme concentrations according to an exemplary embodiment of the present disclosure.

As seen from FIG. 4, when analyzing the photooxidation-induced amplification pattern of the enzyme-substrate reaction products, the detected light emission may be plotted on a graph with, for example, time in the X-axis and relative fluorescence intensity in the Y-axis.

Because the photooxidation-induced amplification is a sort of autocatalytic reaction, it can be plotted as an S-shaped curve according to Equation 1 or can be transformed to a photooxidation-induced amplification model equation of Equation 2.

$$Y = \text{Bottom} + \frac{\text{Top} - \text{Bottom}}{(1 + Qe^{-KX})^{1/S}}$$ [Equation 2]

As indices that represent the photooxidation-induced amplification pattern of the samples, intermediate time (T50), initial time (T10), end time (T90), amplification factor (K), etc. may be used, for example, either alone or in combination. For example, as the characteristic time length (CTL) as an index that represents the photooxidation-induced amplification pattern, T50, T50+T10+T90, K/(0.5/T50)*T50, K/(0.5/T50)*(T50+T10+T90), etc. may be used.

In other words, when analyzing the concentration of the aggregated proteins, the photooxidation-induced amplification after the reaction between the antibody-conjugated enzymes to which the aggregated proteins are bound and the substrates is plotted on a graph of the change in the color or light emission of the products versus time and the body fluid sample containing the aggregated proteins is quantified by extracting indices that represent the photooxidation-induced amplification pattern. As the indices that represent the photooxidation-induced amplification pattern, at least one of intermediate time (T50), initial time (T10), end time (T90) and amplification factor (K) may be used either alone or in combination.

Because the produced amount of resorufin in the early stage increases as the concentration of the antibody-conjugated enzymes to which the aggregated proteins are bound is higher, the rate of the autocatalytic reaction is also fast and the photooxidation-induced amplification proceeds quickly. As a result, the fluorescence intensity is changed quickly. On the other hand, as the concentration of the antibody-conjugated enzymes to which the aggregated proteins are bound is lower, the produced amount of resorufin in the early stage decreases. Therefore, the rate of the autocatalytic reaction is slow and the photooxidation-induced amplification proceeds slowly. As a result, the fluorescence intensity is changed slowly.

Accordingly, the concentration of the antibody-conjugated enzymes can be determined by comparing the relative time of the fluorescence intensity change and the immune reaction can be more accurately analyzed even with samples of low concentration and trace amounts.

Because the photooxidation-induced amplification is affected by the initial amount of resorufin, the contents of the aggregated proteins in the form of oligomers or monomers present in the body fluid sample can be quantified and compared by extracting indices that represent the photooxidation-induced amplification and comparing with a reference value. The reference value may be the index that represents the photooxidation-induced amplification pattern of the reference sample not containing the aggregated proteins.

Figure 5:
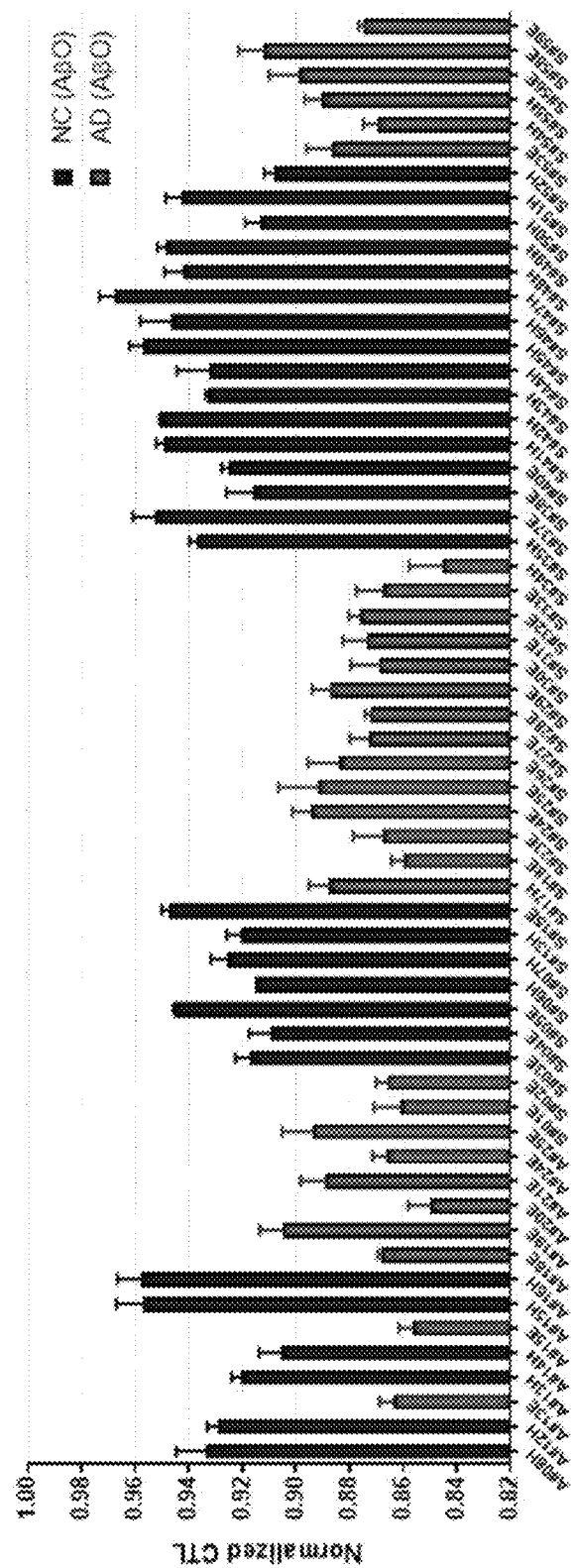
FIG. 5 is a graph showing a result of distinguishing Alzheimer's disease patients from normal people through high-sensitive immunoassay of aggregated oligomer-type β-amyloid proteins extracted from neuronal exosomes in plasma by photooxidation-induced amplification.

FIG. 5 is a graph showing a result of distinguishing Alzheimer's disease patients from normal people through high-sensitive immunoassay of aggregated oligomer-type β-amyloid proteins extracted from neuronal exosomes in plasma by photooxidation-induced amplification.

As seen from FIG. 5, Alzheimer's disease patients can be distinguished from normal people through high-sensitive immunoassay of aggregated oligomer-type β-amyloid proteins extracted from neuronal exosomes in plasma in the body fluid sample by photooxidation-induced amplification.

To describe in detail, samples of neuronal exosomes from plasma of normal people and Alzheimer's disease patients may be prepared as body fluid samples. Then, oligomer-type β-amyloids are selectively detected using 6E10 primary antibodies bound to magnetic beads and peroxidase-conjugated 6E10 as secondary antibodies and an enzyme-substrate reaction is performed.

The photooxidation-induced amplification can be performed on a 96-well plate using a fluorescence microscope and CTL=K/(0.5/T50)*T50, etc. may be used as an index that represents the photooxidation-induced amplification pattern.

Figure 6:
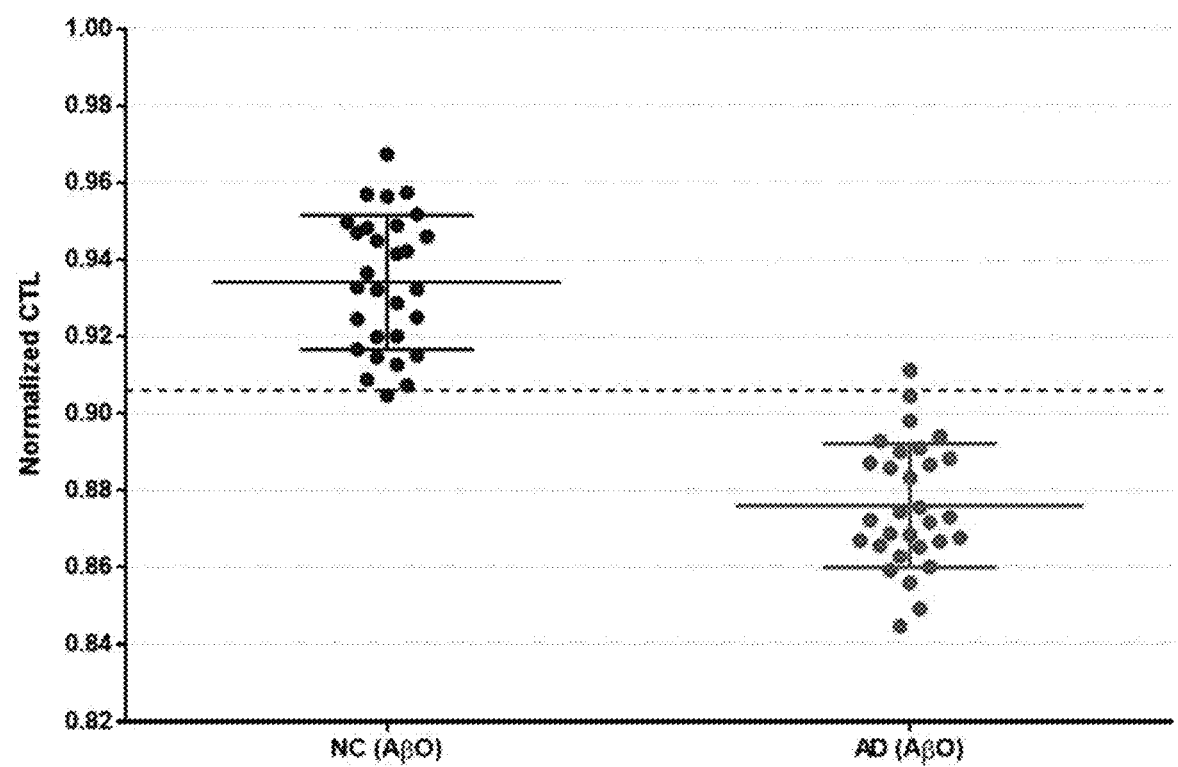
FIG. 6 is another graph showing a result of distinguishing Alzheimer's disease patients from normal people through high-sensitive immunoassay of aggregated oligomer-type β-amyloid proteins extracted from neuronal exosomes in plasma by photooxidation-induced amplification.

FIG. 6 is another graph showing a result of distinguishing Alzheimer's disease patients from normal people through high-sensitive immunoassay of aggregated oligomer-type β-amyloid proteins extracted from neuronal exosomes in plasma by photooxidation-induced amplification. And, FIG. 7 is a ROC curve showing a result of distinguishing Alzheimer's disease patients from normal people through high-sensitive immunoassay of aggregated oligomer-type β-amyloid proteins extracted from neuronal exosomes in plasma by photooxidation-induced amplification.

Figure 7:
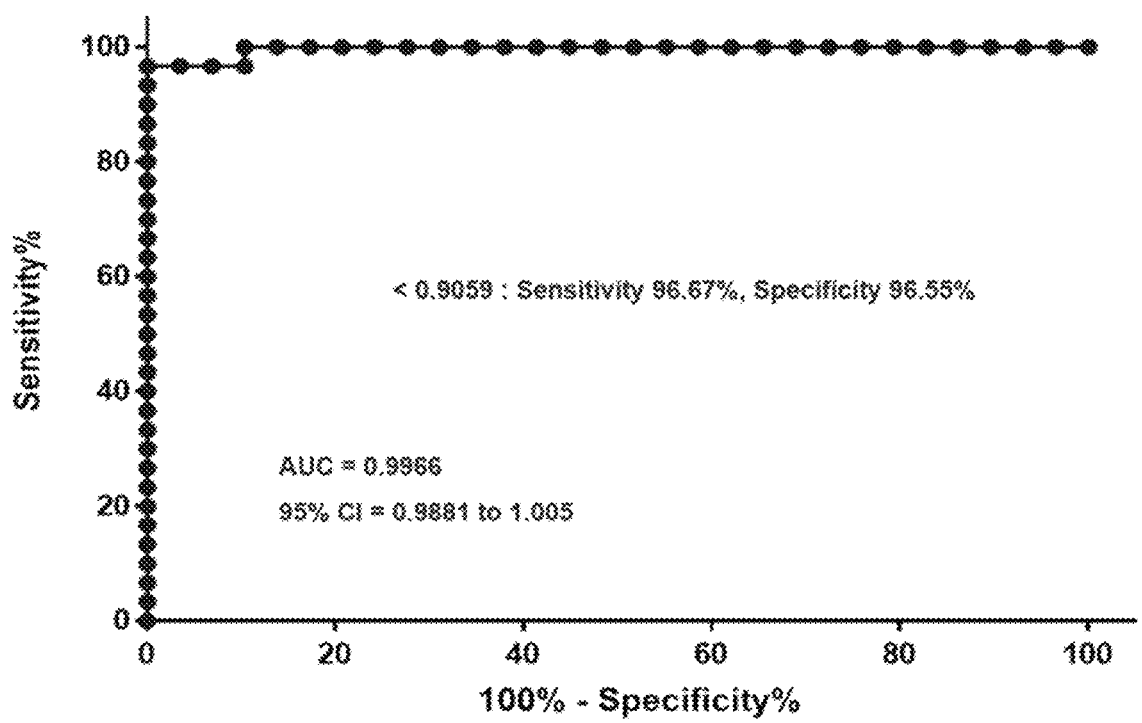
FIG. 7 is a ROC curve showing a result of distinguishing Alzheimer's disease patients from normal people through high-sensitive immunoassay of aggregated oligomer-type β-amyloid proteins extracted from neuronal exosomes in plasma by photooxidation-induced amplification.

Referring to FIG. 6 and FIG. 7, after the photooxidation-induced amplification, Alzheimer's disease patients can be distinguished from normal people with a sensitivity of 96% or higher and a selectivity of 96% or higher by comparing the CTL values of the samples from normal people and Alzheimer's disease patients as the photooxidation-induced amplification pattern indices with the CTL value of a reference sample not containing β-amyloid.

Figure 8:
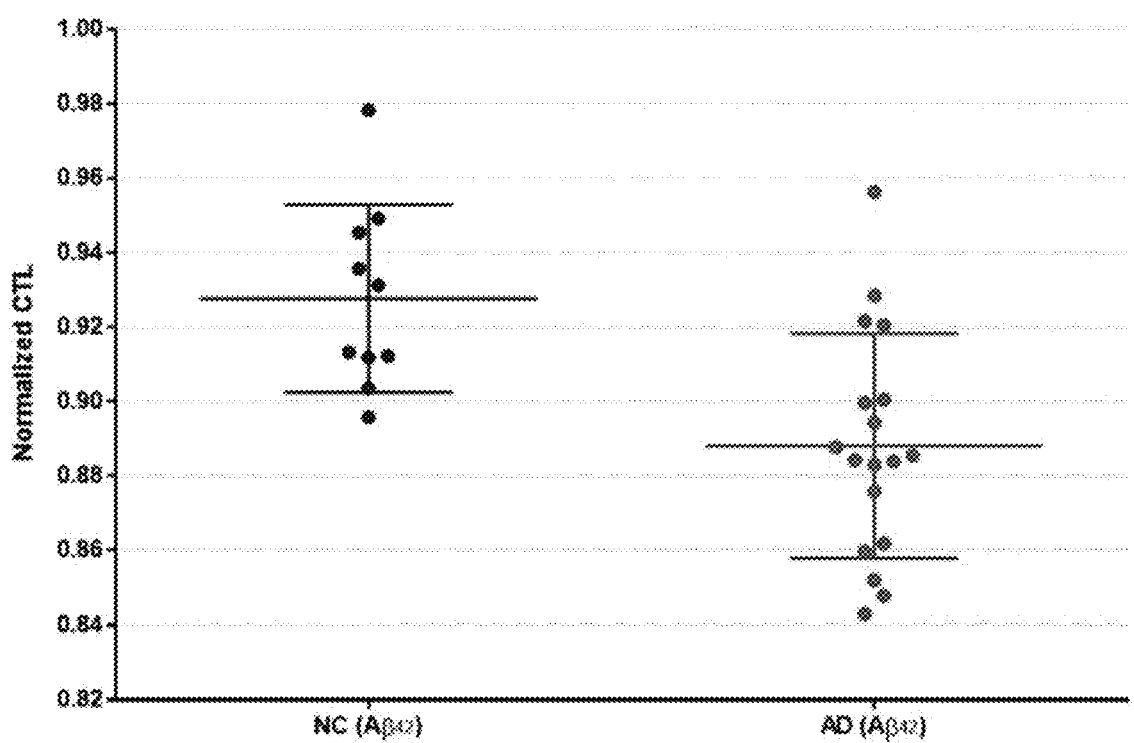
FIG. 8 is a graph showing a result of distinguishing Alzheimer's disease patients from normal people through immunoassay of aggregated monomer-type β-amyloid proteins extracted from neuronal exosomes in plasma by photooxidation-induced amplification.

FIG. 8 is a graph showing a result of distinguishing Alzheimer's disease patients from normal people through immunoassay of aggregated monomer-type β-amyloid proteins extracted from neuronal exosomes in plasma by photooxidation-induced amplification.

As seen from FIG. 8, Alzheimer's disease patients can be distinguished from normal people through high-sensitive immunoassay of aggregated monomer-type β-amyloid proteins extracted from neuronal exosomes in plasma of blood samples by photooxidation-induced amplification.

To describe in detail, samples of neuronal exosomes from plasma of normal people and Alzheimer's disease patients may be prepared as blood samples. Then, monomer-type β-amyloids are selectively detected using 6E10 primary antibodies bound to magnetic beads and peroxidase-conjugated 12F4 as secondary antibodies and an enzyme-substrate reaction is performed.

The photooxidation-induced amplification can be performed on a 96-well plate using a fluorescence microscope and CTL=K/(0.5/T50)*T50, etc. may be used as an index that represents the photooxidation-induced amplification pattern.

Then, Alzheimer's disease patients can be distinguished from normal people by comparing the CTL values of the body fluid samples from normal people and Alzheimer's disease patients with the CTL value of a reference sample not containing β-amyloid.

To compare the measurement result of FIG. 6 with that of FIG. 8, it can be seen that Alzheimer's disease patients can be distinguished from normal people more accurately through high-sensitive immunoassay of aggregated oligomer-type β-amyloid proteins by photooxidation-induced amplification as shown in FIG. 6, although the difference in the CTL values of normal people and Alzheimer's disease patients can be confirmed also through high-sensitive immunoassay of aggregated monomer-type β-amyloid proteins by photooxidation-induced amplification.

The method for neurodegenerative disease diagnosis using high-sensitive immunoassay of aggregated proteins by photooxidation-induced amplification according to the present disclosure allows quantitative analysis of aggregated proteins in the form of oligomers or monomers which are present in trace amounts in a body fluid and measures normal or abnormal protein aggregation by detecting the aggregated proteins in the form of oligomers or monomers with high sensitivity by reaction of antibody-conjugated enzymes selectively bound to the aggregated proteins with substrates and photooxidation-induced amplification, thereby allowing accurate diagnosis of a neurodegenerative disease.

While the present disclosure has been described with respect to the specific embodiments, it will be apparent to those skilled in the art that various changes and modifications may be made without departing from the spirit and scope of the disclosure as defined in the following claims.

What is claimed is:

1. A method for detecting an aggregated protein associated with Alzheimer's disease (AD) in a body fluid sample of a subject, the method comprising:
   (a) preparing a body fluid sample comprising the aggregated protein, wherein the body fluid sample is selected from the group consisting of blood, plasma, serum, saliva, urine, tears and snivel, and wherein the aggregated protein is selected from the group consisting of β-amyloid (amyloid-β) and tau, wherein said preparing comprises the steps of:
      (i) extracting exosomes from the body fluid sample, and isolating neuronal exosomes from the extracted exosomes or lysing the extracted exosomes to prepare a sample to be analyzed;
      (ii) adding the prepared sample of (i) to a solid support or magnetic beads onto which a primary antibody recognizing the N-terminus of the aggregated protein is bound, incubating for a predetermined time and then washing with a buffer solution;
      (iii) incubating with a secondary antibody for a predetermined time and washing with a buffer solution, wherein the secondary antibody is conjugated to an enzyme that can react with a substrate for an enzyme-substrate reaction, and wherein the secondary antibody is selected from the group consisting of an antibody recognizing the N-terminus of the aggregated protein and an antibody recognizing the C-terminus of the aggregated protein;
   (b) preparing a reference sample, wherein the reference sample is a body fluid sample obtained from a subject not having AD;
   (c) performing, in separate reactions, an enzyme-substrate reaction on the prepared body fluid sample (a) and the reference sample (b);
   (d) after the enzyme-substrate reaction, performing photooxidation-induced amplification by continuously exposing the body fluid sample and the reference sample to light;
   (e) optically detecting light emission from products produced during the photo-oxidation-induced amplification, and measuring and recording product light emission intensity as a function of time to generate a pattern of appearance of product over time; and
   (f) analyzing the samples by comparing the pattern generated from the body fluid sample with the pattern generated from the reference sample,
   wherein the analyzing compares the pattern generated from the body fluid sample and the pattern generated from the reference sample at characteristic time lengths (CTLs), each as an index that represents the photooxidation-induced amplification, and uses an amplification factor (K) and at least one of initial time (T10), intermediate time (T50), and end time (T90),
   wherein: T10=the time at which the light emission reaches 10% of its maximum value; T50=the time at which the light emission reaches 50% of its maximum value; T90=the time at which the light emission reaches 90% of its maximum value.

2. The method according to claim 1, wherein the substrate for the enzyme-substrate reaction comprises 10-acetyl-3,7-dihydroxyphenoxazine (ADHP).

3. The method according to claim 1, wherein said performing the photooxidation-induced amplification comprises exposing the body fluid sample and the reference sample continuously to light after the enzyme-substrate reaction, so that the pattern of appearance of product over time is generated according to Equation 1 and the light emission intensity is fluorescence intensity:

$$Y = \frac{AR_0 + RSF_0}{1 + \frac{AR_0}{RSF_0}e^{-(AR_0+RSF_0)\times RX}};$$ [Equation 1]

wherein Y=fluorescence intensity, $AR_o$=substrate initial concentration, RX=reaction constant at time X, $RSF_o$=product initial concentration and X=reaction time.

4. The method according to claim 3, wherein said optically detecting a light emission from the products during the photooxidation-induced amplification comprises continuously measuring the light emission of the products due to the autocatalytic reaction with time while continuously exposing the body fluid sample and the reference sample to light.

5. The method according to claim 3, wherein said continuously exposing to light during the photooxidation-induced amplification comprises continuously exposing to light while recording video images.

6. The method according to claim 1, wherein, the pattern is recorded by indexing, said indexing is performed by plotting the change in a light emission of the detected products versus time on a graph, with the time in the X-axis and the light emission of the detected products in the Y-axis.

7. The method according to claim 6, wherein, in said plotting the photooxidation-induced amplification on a graph, it is plotted on a graph according to Equation 1 or a photooxidation-induced amplification model equation of Equation 2:

$$Y = \text{Bottom} + \frac{\text{Top} - \text{Bottom}}{(1 + Qe^{-KX})^{1/S}} \quad \text{[Equation 2]}$$

wherein Y=fluorescence intensity, "bottom"=minimum intensity, "top"=maximum intensity, K=amplification factor, X=concentration and S=Hill Slope value.

8. The method according to claim 1, wherein said pattern is generated by plotting the appearance of product versus time on a graph; and
   quantifying the amount of aggregated protein by extracting indices that represent the photooxidation-induced amplification pattern and comparing the index of the body fluid sample with the index of the reference sample.

9. The method according to claim 1, wherein the product that appears over time is fluorescent resorufin generated from colorless ADHP.

10. A method for determining an amount of aggregated β-amyloid protein associated with Alzheimer's disease (AD) in a body fluid sample, comprising:
    (a) preparing the body fluid sample for analysis, wherein said preparing comprises:
        (i) obtaining a body fluid sample from a subject suspected of having AD;
        (ii) extracting exosomes from the body fluid sample, and isolating neuronal exosomes from the extracted exosomes or lysing the extracted exosomes to prepare a sample to be analyzed;
        (iii) contacting the prepared sample of (ii) with a peroxidase-conjugated antibody specific for aggregated β-amyloid protein, incubating to allow antibody binding with the aggregated β-amyloid protein, and washing to remove unbound antibody;
        (iv) performing an enzyme-substrate reaction comprising converting ADHP into resorufin;
        (v) after the enzyme-substrate reaction, performing photooxidation-induced amplification of resorufin by continuously exposing the sample to light, and using video images to record an experimental pattern of growth of resorufin light emission as a function of time;
    (b) preparing a reference sample for analysis, wherein said preparing comprises:
        (vi) obtaining a reference body fluid sample from a subject not having AD;
        (vii) contacting the reference sample with a peroxidase-conjugated antibody specific for aggregated β-amyloid protein, incubating to allow antibody binding with the aggregated β-amyloid protein, and washing to remove unbound antibody;
        (viii) performing an enzyme-substrate reaction comprising converting ADHP into resorufin;
        (ix) after the enzyme-substrate reaction, performing photooxidation-induced amplification of resorufin by continuously exposing the sample to light, and using video images to record a reference pattern of growth of resorufin light emission as a function of time;
    (c) analyzing the content of the samples by a comparison of experimental and reference photooxidation-induced amplification reactions,
    wherein the experimental pattern is compared with the reference pattern to determine the amount of aggregated β-amyloid protein in the subject suspected of having AD in comparison to the subject without AD,
    wherein said experimental and reference patterns are compared by generating characteristic time lengths (CTLs), each as an index that represents the photooxidation-induced amplification using at least one of intermediate time (T50), initial time (T10), end time (T90), and amplification factor (K),
    and wherein: T10=the time at which the resorufin light emission reaches 10% of its maximum value; T50=the time at which the resorufin light emission reaches 50% of its maximum value; T90=the time at which the resorufin light emission reaches 90% of its maximum value.

11. The method of claim 10, wherein said experimental and reference patterns are compared by generating graphs of the growth of resorufin light emission as a function of time.

* * * * *